United States Patent [19]

Galindo

[11] 4,411,657
[45] Oct. 25, 1983

[54] HYPODERMIC NEEDLE

[76] Inventor: Anibal Galindo, 6500 Caballero Blvd., Coral Gables, Fla. 33146

[21] Appl. No.: 353,517

[22] Filed: Mar. 1, 1982

Related U.S. Application Data

[63] Continuation of Ser. No. 151,378, May 19, 1980, abandoned.

[51] Int. Cl.³ .............................................. A61M 5/32
[52] U.S. Cl. .................................................... 604/274
[58] Field of Search ................... 128/642, 207.21, 784, 128/419 P

[56] References Cited

U.S. PATENT DOCUMENTS 3,078,850 2/1963 Schein ............................ 128/419 P
3,313,293 4/1973 Chesebrough et al. ............. 128/642
3,727,613 4/1973 Sorenson et al. .................... 604/165

Primary Examiner—William E. Kamm
Attorney, Agent, or Firm—Malin & Haley

[57] ABSTRACT

An improved hypodermic needle to greatly reduce or eliminate trauma to nerve fascicles during the injection of an anesthesia. The needle includes a solid, conically-shaped tip, preferably pointed, an elongated shaft having a hollow interior for delivering the anesthesia and one or more lateral openings strategically spaced away from the tip of the needle. The pinpoint tip of the needle separates the nerve fascicles without cutting them, also preventing intraneural pressurized injection of the anesthesia while allowing for dispensing of the anesthesia in the perineural space. In addition the needle may be used to further localize nerves to be blocked through electrical stimulation. In this embodiment the shaft of the needle has a coating of electrically insulating material or a plastic sleeve while the tip is non-insulated and appropriate circuitry is used in conjunction with the needle so treated. The needle may be withdrawn leaving the plastic sleeve in place to be used to repeat injections and prolong the time of blockage, or to reinforce a difficient block.

5 Claims, 9 Drawing Figures

| NEEDLE TYPE | NUMBER OF PENETRATIONS | NERVE DAMAGE | DIE MIGRATION (DIAMETER) | MEAN PRESSURE NEEDLE ALONE | MEAN PRESSURE INSIDE MUSCLE | MEAN PRESSURE |
|---|---|---|---|---|---|---|
| CONV-ENTIONAL | 17 | 10 | >10mm-10 | 225mm Hg (43) | 435mm Hg (63) | INTRANEURAL (63) 755mm Hg (63) |
| NEW | 21 | 0 | MINIMAL-10 | 218mm Hg (51) | 440mm Hg (52) | PERINEURAL * 281 mm Hg (38) |

HYPODERMIC NEEDLE

This is a continuation of application Ser. No. 151,378, filed May 19, 1980.

BACKGROUND OF THE INVENTION

This invention relates generally to a hypodermic needle that is useful for applying a local anesthetic to block nerve transmission, otherwise known as regional anesthesia.

Conventional hypodermic needles have a blade-like tip for penetrating the flesh, the tip having the orifice through which anesthetic or other liquid is ejected. It has been found that trauma to nerve fascicles results due to the slicing action of the conventional needle tip which literally cuts into the nerves themselves. Any direct intraneural injection resulting from cutting into the nerve and the tremendous fluid pressure through the orifice can result in post block nerve injuries. A study of causes of post anesthetic nerve damage (nerve palsy) suggests three major problems: (1) Direct damage to the nerve by the cutting edge of a conventional needle; (2) Neural trauma by high pressure intraneural injection of a local anesthetic resulting from the cutting and the position of the needle orifice, and (3) the toxic effect of the anesthetic or its perservatives from being subjected directly onto the interior of the nerve.

The present invention overcomes or minimizes the first two possibilities. This is accomplished by utilization of an improved needle tip which does not pierce or slice into the nerve fascicle nor permit an intraneural injection but instead allows for injection in the perineural space between the nerve fascicles.

SUMMARY OF THE INVENTION

A hypodermic needle having an elongated, rigid shaft of a predetermined length and diameter, said shaft including a hollow, interior passage, that terminates prior to the tip of the needle. One end of the needle is fastened to a conventional syringe. The tip end of the needle is a solid, conically-shaped point having predetermined dimensions. Disposed back from the tip are openings along the circumferential body of the needle that are spaced strategically from the tip such that the injection liquid is dispensed at approximately a 90° angle to the longitudinal axis of the needle shaft.

The conical shape and size of the needle tip is such that it will pass between the nerve fascicles rather than slice through them. During the penetration of the needle, the tip, of its shape and size, can force aside individual nerve fascicles, allowing penetration into a given nerve block without cutting. Subsequent dispensing of the anesthesia or other suitable liquids through one or more laterally facing orifices (relative to the needle shaft) greatly reduces the liquid pressure on nerve fascicles immediately surrounding each orifice.

In the preferred embodiment, the improved needle has a pointed conical tip between two to four millimeters long the final one or two millimeters being solid, followed by a plurality of circular orifices at a variable distance of no more than four millimeters from the solid tip, or by an elongated, elliptical opening (0.3 to 0.5 millimeters wide) for ejection of the anesthesia. The initial orifice from the solid tip may be placed either immediately, one millimeter or two millimeters, longitudinally from the point. Two or more orifices for achieving three openings in each needle may be located at one millimeter intervals around the needle circumference, but not in the same axial plane. If the elliptically slotted needle is preferred, slots may be located anywhere between beginning immediately behind the solid point periphery up to two millimeters behind this position. The needle gauges may be varied depending on the type of nerve block to be anesthetized and the particular build of the patient.

EXPERIMENTAL OBSERVATIONS

Experiments were conducted in situ sciatic nerves of anesthesized rabbits. Under direct visual observation, nerves were penetrated at intervals of ten millimeters with a conventional (short bevelled) 22 gauge hypodermic needle. This needle was advanced transversely or perpendicularly over the largest bundle of nerve fascicles. Other nerves were penetrated in a similar manner with a 22 gauge needle constructed in accordance with the present invention described herein. The nerves were bathed for two hours using a solution of five (5) percent bovine albumin tagged with one (1) percent Evans blue as described by Selander et al "Peripheral Nerve Injury Due To Injection Needles Used For Regional Anesthesia" Acta Anesthesia Scand 21:182-188, 1977. Damage to the nerve was assessed by observing and counting under the microscope the number of times that the penetration of the needles cut one or more nerve fascicles; fluorescence microscope, dark field condenser and special lamp were used following Selander et al and Steinwalt and Klatzo "Selected Vulnerability of the Blood-Brain Barrier In Chemically Induced Lesions", J. Neuropath. Exp. neural 25:542-560, 1966.

To other sciatic nerves, intraneural injections of 0.1 cc of 0.1% methylene blue solution was tried 10 times each with a regular short bevelled hypodermic needle and with the improved needle in accordance with this invention, both 0.7 millimeters in diameter (22 gauge). The degree of penetration of the anesthetic solution into the nerve was graded as (1) minimal, (2) penetration in a radius of less than 10 millimeters, and (3) penetration with a migration of more than 10 milimeters. Results of the observations are embodied in Table 1 of FIG. 8. Fluid pressures of injection through the needle alone when the tip was located inside the muscle, the perineural space, and the nerve were measured using a constant infusion pump to inject a normal saline solution contained in a 50 cc syringe and delivered at a speed of 15.3 cc's per minute for a maximum of 4 seconds. A Stathan pressure transducer connected to a two-channel graph recorder was used for pressure determination.

To summarize the results and conclusions, it can be seen from Table 8 that the penetration damage to the nerve using the improved hypodermic needle is greatly reduced and eliminated. Using the improved needle, in accordance with the present invention, the die could not be injected inside the nerve but was ejected through orifices or (part of the slot) outside of the nerve thus the pressure of injection with the tip of the needle inside the nerve was approximately 400 millimeters Hg lower with the needle in accordance with the present invention which was injecting perineurally than with the conventional needle that was injecting intraneurally.

In an alternate embodiment the improved needle in accordance with the principles of the invention can be modified for use to localize electrically the nerves to be blocked through mild electrical stimulation. In this embodiment the shaft of the needle (but not the tip) is coated with a fine (0.01 milimeter) film of tygon (or other comparable insulating material) or a plastic sleeve placed for the same purposes along the shaft of the needle, leaving the solid tip bare. The plastic sleeve may be left in-situ after withdrawing the needle; this would allow repeated injections of the anesthetic. A small five millimeter bar or small wings are built into the hub of the needle to facilitate wiring to a nerve stimulator; the circuit is closed through a cable connecting the skin to the stimulator's ground. With proper auxiliary equipment the insulated needle can be used as a stimulating or recording electrode to perform precise injection of local anesthetic solutions.

It is an object of this invention to provide an improved hypodermic needle for use with a conventional syringe that reduces or eliminates trauma or damage to the nerve.

It is another object of this invention to provide an improved hypodermic needle which prevents cutting or traumatic nerve fascicles by intraneural injection of local anesthetics.

And yet still another object of this invention is to provide an improved hypodermic needle that reduces the pressure adjacent to the surrounding tissue when administering a local anesthesia by providing for perineural dispensing rather than intraneural dispensing of the anesthesia.

But yet still another object of this invention is to provide a hypodermic needle having a solid, pointed tip, with the fluid ejection orifices being disposed to eject fluid perpendicular to the longitudinal axis of the needle body.

In accordance with these and other objects which will be apparent hereinafter, the instant invention will now be described with particular reference to the accompanying drawings.

BRIEF DESCRIPTION OF THE DRAWINGS

FIG. 8 shows a table comparing experimental results between a conventional hypodermic needle and a needle constructed in accordance with the present invention.

DESCRIPTION OF THE PREFERRED EMBODIMENT

Figure 1:
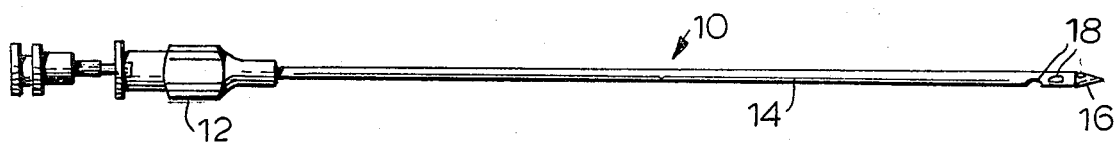
FIG. 1 shows a side elevational view of the present invention.
Figure 2:
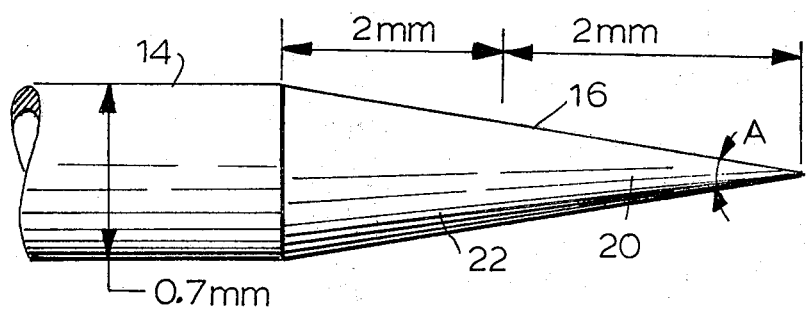
FIG. 2 shows a side elevational, fragmentary view of a needle tip in accordance with the present invention.

Referring now to the drawings and particularly to FIG. 1, the new and improved hypodermic needle is shown generally at 10. The hypodermic needle 10 comprises a hub 12, a hollow, elongated, rigid shaft 14, with a plurality of holes 18 near the tip end 16. The tip end 16 has a conically shaped point which can be introduced into the nerve without causing damage to the nerve. As shown in FIG. 2 the tip end 16 is comprised of a solid portion with a conically shaped point 20 and a hollow portion 22. The design of the tip end 16 with a solid point 20 enables it to force aside individual nerve fascicles allowing penetration to a given nerve without cutting the nerve. The needle 10 has a sharp pinpoint of two to four millimeters in length with a solid portion (cone-shaped) being one or two millimeters in length. The angle of the cone-shaped portion may vary between 90° maximum and 6° minimum. The diameter of the hollow elongated shaft 14 is 0.3 millimeters or 0.7 millimeters depending upon the application.

Figure 3:
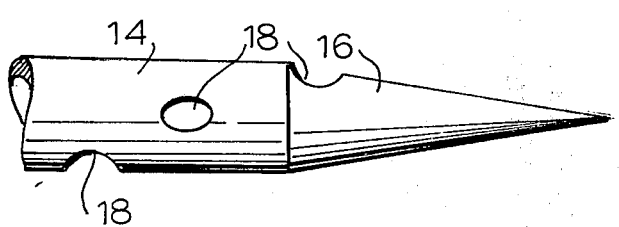
FIG. 3 shows a fragmentary side elevational view of a needle tip in accordance with the present invention.
Figure 5:
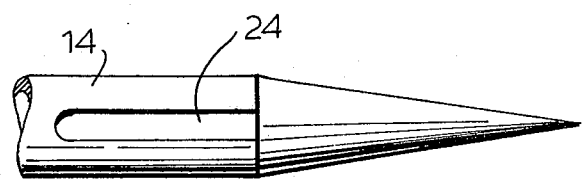
FIG. 5 shows an alternate embodiment of the present invention in a side elevational fragmentary view.
Figure 4:
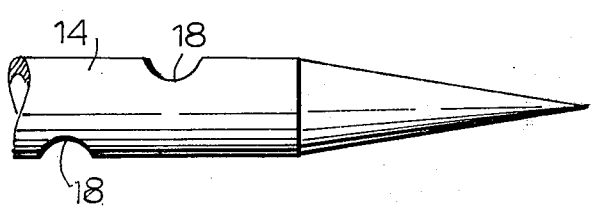
FIG. 4 shows a side elevational view of a hypodermic needle constructed in accordance with the view of FIG. 3 with the axis rotated 90° of the shaft.
Figure 6:
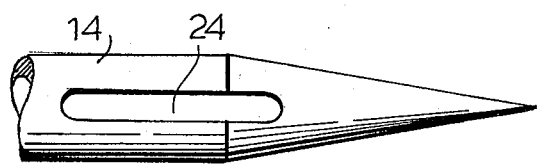
FIG. 6 shows yet another alternate embodiment of the present invention in a side elevational view.

Referring now to FIGS. 3, 4, 5, and 6 various designs of passages to allow the passage of fluids from the needle into the body are shown. In FIGS. 3 and 4, a plurality of holes at a variable distance but no more than four millimeters from the solid tip are shown. The positions of the holes 18 enable the fluid to be injected paraneurally rather than intraneurally as accidentally has been done in the past, since the presence of the nerve over one or more of the holes keeps the fluid from passing therethrough and causes the fluid to be released through one or more of the remaining holes 18 which are not across the nerve. The same problem can be solved also by using an elongated eliptically shaped slot which is normally from 0.3 to 0.5 millimeters in width for injecting the fluid. Again the portion of the elongated slot which is in the nerve will not allow passage of the fluid into the nerve because of the pressure of the nerve thereon and thus the fluid will be injected paraneurally rather than intraneurally. The slot 24 will be located beginning immediately behind the solid point 20 or up to two millimeters behind this point.

Figures 7, 9:
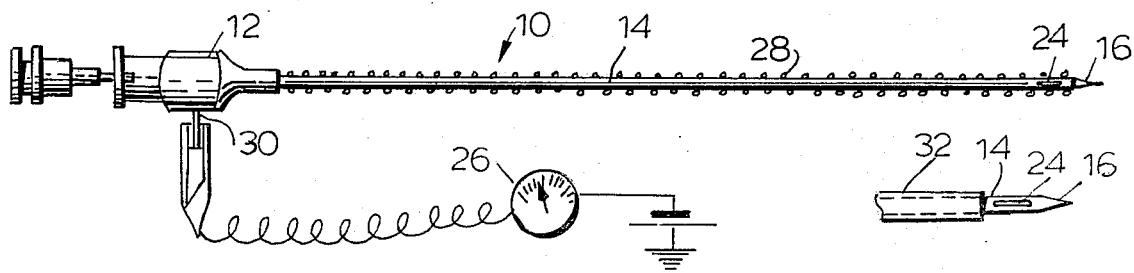
FIG. 7 shows an alternate embodiment of the present invention utilizing and providing electrical stimulation.
FIG. 9 shows a fragmentary plastic sleeve covering the shaft of the needle.

Referring now to FIG. 7, the hypodermic needle 10 can be modified for use to localize electrically the nerves to be blocked by mild electrical stimulation. The shaft 14 of the needle 10 is coated with a fine (0.01 millimeter) film of tygon or other comparable insulating material along the shaft of the needle 10 leaving the solid tip 16 non-insulated. A small 5 millimeter bar 30 or small wings are built into the hub to facilitate connection to a nerve stimulator 26. The nerve stimulator circuit 26 is closed through a cable connecting the skin to the stimulator's ground. With proper auxilliary equipment, the insulated needle 14 can be used as a stimulating or a recording electrode to perform precise injection of local anesthetic solutions.

As shown in FIG. 9, a plastic sleeve may also be used to insulate the needle 14. The plastic sleeve 32 is slidably engaged with the needle 14 and may be left in-situ after withdrawing the needle, thus allowing repeated injections of the local anesthetic or to reinforce a difficult block.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A new and improved nerve anesthesia needle for reducing or eliminating trauma to nerve fascicles during the injection of an anesthesia, comprising:

a hub;

an elongated, rigid electrically conductive shaft of predetermined length and diameter, said shaft having one end connected to said hub; said shaft includes a fluid conduit means for transporting anesthesia to a nerve;

said shaft having a smooth pointed cone-shaped tip means connected to said shaft, said smooth tip means for penetrating without cutting nerves and for locating the nerve through electrical conductivity of said shaft and for paraneurally depositing anesthesia at the located nerve;

said smooth tip means including only a penetrating point for preventing cutting of the nerve;

dispensing means connected to said conduit means for allowing fluid to be dispensed from said shaft, said dispensing means for dispensing anesthesia paraneurally, said dispensing means spaced from said point and including exit opening area means for preventing nerve damage.

2. A new and improved nerve anesthesia needle as set forth in claim 1, wherein:

said dispensing means is an elongated, longitudinal opening in said needle positioned rearward of said smooth tip means.

3. A new and improved nerve anesthesia needle as set forth in claim 1, wherein:

said dispensing means includes a plurality of holes longitudinally disposed along said needle, each said hole spaced from an adjacent hole such that at least one hole allows paraneural injection of said anesthesia for preventing nerve damage, while preventing intraneural injection.

4. A new and improved nerve anesthesia needle as set forth in claims 2 or 3 wherein:

said dispensing means is at least two millimeters from said point.

5. A new and improved nerve anesthesia needle as set forth in claims 2, 3 or 4 including:

an insulation coating on said shaft up to said smooth tip means to insulate said shaft.

* * * * *